United States Patent [19]

Chen

[11] Patent Number: 5,662,737
[45] Date of Patent: Sep. 2, 1997

[54] METHOD FOR MAKING RARE EARTH METAL OXIDE CERAMIC PRECURSOR COMPOUNDS AND USE THEREOF

[75] Inventor: Kuo-Chun Chen, Encinitas, Calif.

[73] Assignee: Quantum Group, Inc., San Diego, Calif.

[21] Appl. No.: 645,105

[22] Filed: May 13, 1996

[51] Int. Cl.$^6$ .................... C07F 5/00; C09K 3/00
[52] U.S. Cl. ........................ 106/287.18; 136/253
[58] Field of Search .................. 106/287.18; 136/253

[56] References Cited

U.S. PATENT DOCUMENTS

| | | | |
|---|---|---|---|
| 3,082,051 | 3/1963 | Wainer et al. | 18/48 |
| 3,082,099 | 3/1963 | Beasley et al. | 106/39 |
| 3,278,571 | 10/1966 | Mazdiyasni et al. | 260/429.2 |
| 4,960,466 | 10/1990 | Koplick | 106/1.29 |
| 4,968,498 | 11/1990 | Wautier et al. | 423/593 |
| 5,001,110 | 3/1991 | Nonake et al. | 505/1 |
| 5,006,508 | 4/1991 | Treacy et al. | 505/1 |
| 5,100,871 | 3/1992 | Chen et al. | 505/1 |
| 5,122,510 | 6/1992 | Chen et al. | 505/1 |
| 5,217,754 | 6/1993 | Santiago-Aviles | 427/226 |
| 5,227,199 | 7/1993 | Hazlebeck et al. | 427/376.2 |
| 5,252,314 | 10/1993 | DeGuire et al. | 423/593 |
| 5,278,135 | 1/1994 | Howard, Jr. et al. | 505/1 |
| 5,281,131 | 1/1994 | Goldstein | 431/253 |
| 5,294,599 | 3/1994 | Shibata et al. | 505/1 |
| 5,304,533 | 4/1994 | Kobayashi et al. | 505/440 |
| 5,312,613 | 5/1994 | Shyu et al. | 423/608 |
| 5,348,918 | 9/1994 | Budd et al. | 501/95 |
| 5,352,642 | 10/1994 | Pak et al. | 501/95 |
| 5,378,665 | 1/1995 | Chen et al. | 501/95 |
| 5,407,618 | 4/1995 | Stephenson | 264/63 |
| 5,516,363 | 5/1996 | Azuma et al. | 106/287.18 |

*Primary Examiner*—David Brunsman
*Attorney, Agent, or Firm*—Christie, Parker & Hale, LLP

[57] ABSTRACT

A method for making rare earth metal oxide ceramic precursor composition comprising reacting a rare earth metal alkoxide with a complexing agent to give a mixture of complexing agent/alkoxide rare earth metal complexes is disclosed. The mixture is hydrolyzed and the precursor composition is isolated. Solubility of the precursor composition in non-polar or polar solvents is affected by the selection of complexing agent amongst other factors. At least partial dissolution of the precursor composition in a solvent gives a preceramic liquid which upon evaporation of the solvent and heating gives a rare earth metal oxide ceramic. Utility of the preceramic liquid include the formation of rare earth metal oxide fibers, thin films, coatings, foams, powders, cast or molded objects or it may be used as a ceramic adhesive.

12 Claims, No Drawings

METHOD FOR MAKING RARE EARTH METAL OXIDE CERAMIC PRECURSOR COMPOUNDS AND USE THEREOF

BACKGROUND

The generation of electricity by thermophotovoltaic (TPV) devices has been an area of intense research in the past few years. Generally, TPV systems combust natural gas or other fossil fuels to thermally stimulate the emission of photons (i.e. light) from an emitter structure. The light generated by the emitter structure is absorbed by photocells which in turn generate electricity. Several U.S. Patents describe TPV devices, for example see U.S. Pat. Nos.: 4,584,426; 4,597,734; 4,776,895; 4,906,178; 5,137,583; 5,281,131; 5,356,487; 5,360,490; 5,383,976; 5,403,405; 5,439,532; 5,500,054; and, 5,503,685.

Presently there are several limitations to the development of highly efficient TPV devices including: (1) accommodating the extremely high operating temperatures without the emitter structure melting or degrading; (2) increasing the photon content of specific peak spectral emissions from the emitter; (3) reducing the capital cost of TPV units verses the capital cost of conventional electricity generating means; and, (4) reducing the photovoltaic current collection or power density limitations of the photocells.

The development of high temperature "superemissive" ceramic materials for use in the emitter structure has been proposed as a solution to the first three of the above mentioned limitations.

The term "superemissive material" as used herein, refers to a material that when heated above a threshold temperature, emits photons in relatively narrow and discrete spectral bands. In contrast, blackbody or greybody materials, when heated emit photons in broad spectral bands, the peak wavelength of which depends on the temperature to which the material has been heated. Examples of superemissive materials include: rare earth oxides, and mixtures of rare earth oxides. Especially useful for the manufacturing of TPV emitter structures are superemitter ceramic fibers of the rare earth oxides and mixtures thereof.

An example of the use of rare earth oxide superemitter fibers in a TPV device is contained in U.S. Pat. No. 5,356,487 in which Goldstein et al. disclose the use of superemissive burners to improve the efficiency of electrical generation in TPV devices. The disclosed burner structures are made using a "relic" process and tend to be fragile and rigid once formed. Essentially, the same method is disclosed by Goldstein in U.S. Pat. Nos. 4,776,895; 4,906,178; and 5,400,765.

Heating metal oxide compositions to generate light is an old technology and is disclosed in several pre-1900 patents, for example see U.S. Pat. Nos.: 359,524; 409,529; 563,524; 575,261; or, 614,556. The principle focus of this early work involves compositions containing thorium oxide with various amounts of other metal oxides being formed into mantles for use in gas lighting. The role of the additional oxides is to change the "color" of the light emitted by the mantle and typically include cerium oxide, yttrium oxide, strontium oxide, lanthanum oxide, uranium oxide, etc. In fact this technology is still in use today in the form of mantles for gas powered camping lanterns. As is well known to those who have used these devices, these mantles are very fragile and cannot be subjected to shock or handling without damage.

The "relic" process, previously mentioned above, is the most commonly used method of making rare earth metal oxide fibers and articles. Generally described, the relic process involves soaking a template made of carbon containing compounds, such as rayon or nylon cloth, in a solution containing a metal salt. The soaked template is dried and heated under carefully controlled conditions to oxidize or "burn-out" the carbon containing compounds that make up the template thus leaving behind a fragile metal oxide structure. The physical properties of the final product are influenced by a variety of factors such as, the metal salts used and their concentration in solution, the duration of the soaking time; the selection of the material for the template, the atmospheric and temperature conditions of the "burn-out" step; the atmospheric and temperature conditions of any subsequent heat treatments. Most importantly, the relic process produces a rare earth metal oxide fiber that has taken the shape and form of the template fibers. Typically these rayon and nylon fibers are short, irregular in shape and have variable surface morphologies. Therefore, although the relic process is easy to carry out, the quality of the final product is of variable quality and lacks uniformity and strength needed for TPV applications.

Therefore, there is a continuing need for new methods of making rare earth oxide superemissive materials that are suitable for use in the emitter structures of TPV devices. These superemissive materials should be able to withstand long term exposure to the high temperature, oxidizing environment encountered in the TPV combustion chamber; emit photons within a narrow wavelength distribution; be able to withstand the rigors of handling and transporting the TPV device; and, yet be simple and economical to make.

BRIEF DESCRIPTION OF THE INVENTION

The present invention is directed to a new and novel method of making rare earth metal oxide ceramic precursor compositions, the compositions themselves and methods of using the precursor composisions to make rare earth metal oxide ceramics. Precursor compositions are made by reacting rare earth metal alkoxides with a complexing agent to give a mixture of complexing agent-alkoxide rare earth metal complexes, hydrolyzing said complexes and isolating the rare earth metal oxide ceramic precursor composition. Rare earth metal alkoxides that may be used in this process include rare earth metals selected from the group including cerium, praseodymium, neodymium, promethium, samarium, thulium, ytterbium, lutetium, and mixtures thereof and alkoxides selected from the group including straight chain, branched, and cyclic primary alkoxides having from 1 to 6 carbon atoms, straight chain, branched, and cyclic secondary alkoxides having from 3 to 8 carbon atoms, and branched and cyclic tertiary alkoxides having from 4 to 8 carbon atoms. The reaction solvent is preferably the alcohol corresponding to the alkoxide portion of the rare earth metal alkoxide.

The precursor composition is at least partially soluble in either polar or non-polar solvents to give a preceramic liquid. Solubility primarily depends upon the choice of complexing agent, however other factors affect solubility or lack thereof. When the complexing agent is 2-ethylhexanoic acid, a precursor composition is made that is soluble in non-polar solvents. However, triethanolamine is the complexing agent, the resulting precursor composition is soluble in polar solvents. The viscosity of the preceramic liquid primarily depends upon the weight to weight ratio of the precursor composition to solvent that make up the preceramic liquid.

Upon evaporation of the solvent from the preceramic liquid, a green ceramic is formed which upon heat treatment becomes a rare earth metal oxide ceramic object having the general shape of the green ceramic. A number of other various uses for the preceramic liquid are possible including the formation of fibers, thin films, coatings, foams, solid objects, powders etc., with several exemplary embodiments being disclosed herein.

DETAILED DESCRIPTION

The following terms and words are used herein and are defined to mean the following:

"preceramic liquid" is the precursor composition that has been at least partially dissolved in a solvent;

"green ceramic" is a solidified state of the preceramic liquid that is ready to be burnt-out;

"burn-out" is the process in which controlled oxidation is used to remove carbon containing compounds from the green ceramic and results in an ceramic structure that is ready to be sintered;

"sinter" is the process in which a burnt-out ceramic is heated to high temperature to relieve internal stresses, and to strengthen and solidify the rare earth metal oxide ceramic structure;

The present application is directed to a new method of making rare earth oxide ceramic articles, such as fibers, thin films, coatings and bulk objects using a precursor composition. The precursor composition can also be used as an adhesive for the cementing together of rare earth metal oxide ceramics without the introduction of other components or elements. Although this application is primarily focused on the use of the precursor and preceramic liquids in the field of TPV, one skilled in the art would appreciate that other uses exist where the properties of rare earth metal oxide ceramics are desired. Such uses include, but are not limited to: electro-luminescent elements and displays, colored "heads-up" displays, laser pumping devices, photochemical reactors, and so on.

The precursor composition of the present invention is unlike prior art metal alkoxide precursors which are very moisture sensitive and rely upon an irreversible sol to gel transition to control viscosity. In contrast, exposure of the precursor composition of the present invention to typical laboratory conditions of temperature and relative humidity does not cause reaction. Therefore, the powdered precursor composition can be simply stored in screw cap jars until needed. The solubility properties of the powdered precursor composition are readily varied so that preceramic liquids can be made using non-polar solvents or polar solvents. The viscosity properties of these preceramic liquid can also be varied, so that viscosity can span the range between free-flowing solutions to viscous solutions to damp solid pastes. The preceramic liquid is unaffected by exposure to air or moisture. However, upon the evaporation of the solvent it will harden into a green ceramic of the shape given to it.

The rare earth alkoxides used in the process of making the precursor composition of the present invention may be formed in the reaction of the rare earth metal with an alcohol solvent/reagent as described in U.S. Pat. No. 3,278,571, the contents of which are hereby incorporated by reference. For example, solutions of ytterbium isopropoxide in isopropanol (2-propanol) are made by reacting small pieces of clean, dry ytterbium metal in dry, boiling isopropanol. Since the alkoxide product of the reaction is moisture sensitive, the reaction is typically carried out in a dry nitrogen atmospheric chamber (e.g., a nitrogen "dry" box) or by using well known "Schlenk" techniques for handling air and moisture sensitive materials. The completion of the reaction is assisted by the addition of catalytic amounts of mercury halide, in particular mercury chloride. A clear moisture sensitive solution of ytterbium isopropoxide in isopropanol is obtained upon completion of the reaction by filtering the reaction product to remove the mercury halide and other insoluble solids.

Although the above example uses ytterbium metal and isopropanol to give ytterbium isopropoxide in isopropanol, other rare earth metals and other sources of alkoxide may be used give substantially the same rare earth alkoxide solution. Therefore, one skilled in the art would know that rare earth metal alkoxides wherein the rare earth metal is selected from the group including, cerium, praseodymium, neodymium, promethium, samarium, europium, gadolinium, terbium, dysprosium, holmium, erbium, thulium, ytterbium, lutetium, and mixtures thereof and the alkoxide is selected from the group of alkoxides including, straight chain, branched, and cyclic primary alkoxides having from 1 to 6 carbon atoms; straight chain, branched or cyclic secondary alkoxides having from 3 to 8 carbon atoms; branched and cyclic tertiary alkoxides having from 4 to 8 carbon atoms; and, mixtures thereof, are within the scope of the present invention. The isopropanol solvent may also be replaced by other alcohol solvents including, straight chain, branched and cyclic primary alcohols having from 3 to 8 carbon atoms; straight chain, branched and cyclic secondary alcohols having from 3 to 8 carbon atoms; branched and cyclic tertiary alcohols having from 4 to 8 carbon atoms; and, mixtures thereof. Preferably the combination of alkoxide/alcohol solvent correspond to one another as in the above example. However, this need not always be the case and therefore should not be construed as a limitation to the many combinations possible and contemplated herein. The use of a rare earth metal secondary alkoxide/secondary alcohol solvent combination is preferred and a rare earth metal isopropoxide/isopropanol combination is more preferred.

The precursor composition of the present invention is made in a series of chemical reactions and manipulations as generally described below. Unless otherwise noted, standard laboratory techniques are used under ambient conditions of temperature and humidity and all chemicals and solvents are of laboratory grade, although, higher or lower grades may be used.

Calculated amounts of rare earth metal alkoxide solution having precisely determined concentrations are measured by weight and combined to give a mixture of rare earth metal alkoxides containing the molar ratio of rare earth elements desired in the final ceramic product. The rare earth metal alkoxides are thoroughly mixed by heating the solution to reflux under dry nitrogen for one or more hours, although, other methods that achieve a homogeneous solution may be used.

A complexing agent is then added to the homogeneous mixture of rare earth metal alkoxides in order replace some, but not all, of the alkoxy groups surrounding the rare earth metal ion in solution. Typically upon addition of the complexing agent a precipitate forms thus giving a solution/suspension mixture. In a preferred embodiment, at least 60 weight percent of a non-polar solvent, such as hexane or cyclohexane, is added to the alkoxide solution before the addition of the complexing agent to prevent the formation of a precipitate.

The chemical reaction taking place upon addition of the complexing agent is believed to give a solution/suspension containing a complex mixture of rare earth metal coordination compounds in which complexing agent and alkoxide serve as ligands. One role of the complexing agent is to partially replace the alkoxide groups surrounding the rare earth metal ion in solution thereby moderating the subsequent hydrolysis process. An additional role of the complexing agent is to help control the solubility and rheological properties of the preceramic liquid and the pyrolysis characteristics of the green ceramic. A large variety of organic compounds that coordinate rare earth metal ions may be used as the complexing agent as long as they substantially achieve the above stated goals in substantially the same manner.

One preferred complexing agent is 2-ethylhexanoic acid, which preferably is added by dilution in the solvent already present in the alkoxide/alcohol mixture. The molar ratio of 2-ethylhexanoic acid added to the total molar amount of the rare earth metal alkoxide is preferably in the range between about 1:1 to 3:1 and more preferably in the range between about 1.5:1 to 2.5:1. These ratio ranges have been optimized to give a precursor composition that is at least partially soluble in non-polar organic solvents to give a preceramic liquid that has suitable viscoelastic properties, and gives a strong, uniform rare earth metal oxide ceramic after being burnt-out and sintered.

Triethanolamine is another preferred complexing agent and gives precursor composition that is soluble in polar solvents, such as water. When triethanolamine is the complexing agent, the ratio of complexing agent: rare earth metal alkoxide is preferably in the range between about 1:1 to 3:1 and more preferably in the range between about 1.5:1 to 2.5:1. These ratio ranges have been optimized to give a precursor composition that is at least partially soluble and produces a preceramic liquid that gives a strong, uniform rare earth metal oxide ceramic after being burnt-out and sintered.

Upon completion of the reaction between the complexing agent and the metal alkoxide, the mixture of complexing agent-alkoxide rare earth metal compounds is reacted with water to hydrolyze the remaining alkoxide groups. The molar amount of water required is preferably in the range between about 0.5 and about 1.5. Typically the water is diluted in dry alcohol and then added to the suspension/solution of complexing agent-alkoxide rare earth metal complexes. Condensation of the hydrolysis product occurs and the rare earth metal oxide ceramic precursor composition is formed.

Isolation of the precursor composition is affected by the removal of solvent, such as by rotary evaporation, until a solid forms. Trace amounts of reaction solvent usually remain which may adversely influence the rheological properties of the preceramic liquid. When 2-ethylhexanoic acid is the complexing agent, the resulting solid cake or layer is preferably redissolved in a second solvent such as a non-polar hydrocarbon solvent cyclohexane, hexane, benzene, toluene, pentane, etc.), to give a viscous clear solution. Warming the solution to between about 50° and 60° C. facilitates the dissolution process. The second solvent is completely removed thus giving a brittle solid product. The precursor composition is preferably pulverized into a fine powder which aids in the latter formation of the preceramic liquid.

In a preferred embodiment of the present invention, the powdered precursor composition is heat treated under compressed nitrogen or argon or air. Such treatment is typically carried out by heating the powder in a furnace at temperatures in the range between about 180° to 300° C. for between about 0.5 to 24 hours and preferably between 200° to 220° C. for between about 4 to 12 hours. After heat treatment the precursor composition powder appears slightly darker in color. The heat treatment step is believed to increase the degree of condensation within the precursor composition. This increased condensation affects solubility of the precursor composition and the rheological properties of the subsequently made preceramic liquid. In the preceramic liquids used in high speed fiber spinning, a heat treated precursor composition is preferred.

The following specific examples of how to make precursor compositions are intended to illustrate and clarify the present invention and are not intended to limit or otherwise restrict the scope of the invention which is defined by the claims. All reactions were carried out using standard laboratory procedures and techniques under ambient laboratory conditions, unless otherwise noted. All chemical reagents were of standard laboratory grade or higher and are readily available from a variety of commercial laboratory chemical suppliers.

Example 1: Preparation of a Precursor Composition for Making Ytterbium Oxide Ceramics. Under a dry, inert atmosphere (i.e. nitrogen) 631.0 g of a 0.400M ytterbium isopropoxide/isopropanol solution was placed in a 1 liter three-neck round bottom flask fitted with a reflux condenser and was stirred and heated to reflux for 1 hour. To this refluxing solution, 34.0 g 2-ethylhexanoic acid in 200 ml of dry isopropanol was added dropwise. The reaction mixture becomes translucent and then eventually turns into a milky white suspension. The solution/suspension was refluxed for 1 hour and then 4.230 g of water diluted in 100 ml dry isopropanol was added dropwise followed by an additional hour of refluxing. The flask was allowed to cool to room temperature and the solvent was removed using vacuum rotary evaporation in air. Upon removal of virtually all of the reaction solvent, a white solid layer is isolated on the container walls. This white solid was dissolved in 50 ml hexane to give a clear, yellowish, viscous solution. The solution was transferred to an open evaporating dish, such as a large petri dish, and the solvent was allowed to evaporate. The resulting brittle mass was pulverized in a mortar and pestle to give the powdered precursor composition. This precursor composition is soluble in a variety of non-polar solvents such as pentane, hexane, cyclohexane, benzene, toluene, xylanes, octane, cyclooctane, and other similar solvents Example 2: Preparation of Heat Treated Precursor Compositions for Making Ytterbium Oxide Ceramics. A powdered precursor composition was prepared by following the steps of the above Example 1. Portions of the powder were heat treated in either air or nitrogen atmospheres for varying amounts of time and temperature. The solubility and the rheological properties of the powders in cyclohexane are given in Table 1.

TABLE 1

Affect of Heat Treatment Conditions on the Solubility and Rheology of a Precursor Composition

| Atmosphere | Temp. (°C.) | Time (hrs) | Solubility and Rheology in cyclohexane |
|---|---|---|---|
| Air | 200 | 4 | soluble, viscous |
| Air | 200 | 8 | soluble, viscous |
| Air | 200 | 12 | soluble, viscous |
| Air | 220 | 4 | partially soluble, viscoelastic |
| Air | 220 | 8 | partially soluble, viscoelastic |
| Air | 250 | 4 | insoluble |
| Air | 250 | 8 | insoluble |
| Air | 250 | 12 | insoluble |

TABLE 1-continued

Affect of Heat Treatment Conditions on the
Solubility and Rheology of a Precursor Composition

| Atmosphere | Temp. (°C.) | Time (hrs) | Solubility and Rheology in cyclohexane |
|---|---|---|---|
| Air | 300 | 2 | insoluble |
| $N_2$ | 200 | 4 | soluble, viscous |
| $N_2$ | 200 | 8 | soluble, viscous |
| $N_2$ | 220 | 0.5 | soluble, viscous |
| $N_2$ | 220 | 1 | soluble, viscous |
| $N_2$ | 220 | 2 | soluble, viscoelastic |
| $N_2$ | 220 | 4 | partially soluble, viscoelastic |
| $N_2$ | 220 | 8 | partially soluble, viscoelastic |

Example 3: Preparation of a Precursor Composition for Making Ytterbium Oxide Ceramics. Under a dry, inert atmosphere (i.e. nitrogen) 44.8 g of a 0.443M ytterbium isoproproxide/isopropanol solution was placed in a 500 ml three-neck round bottom flask fitted with a reflux Condenser and was stirred. To this solution 67.24 g of dry hexane was added so that the weight ratio of hexane to isopropanol is about 1.71:1. The mixture was heated to reflux and 3.38 g 2-ethylhexanoic acid was added. The reaction mixture remains clear and then eventually turns into a viscous solution. The solution was refluxed for ½ hour and then 0.4212 g of water was added dropwise followed by an additional half hour of refluxing. The viscosity of the solution appears to decrease over time during this process. The solvent was removed using vacuum rotary evaporation in air and upon removal of virtually all of the reaction solvent, a clear solid layer is isolated on the container walls. This solid was dissolved in 20 ml hexane to give a clear, yellowish, viscous solution. The solution was transferred to an open evaporating dish, such as a large petri dish, and the solvent was allowed to completely evaporate under ambient conditions. The resulting brittle mass was pulverized in a mortar and pestle to give the powdered precursor composition that is soluble in a variety of non-polar solvents.

Example 4: Preparation of a Polar Solvent Soluble Precursor Composition for Making Ytterbium Oxide Ceramics. Under a dry, inert atmosphere (i.e. nitrogen) 59.97 g of a 0.400M ytterbium isoproproxide/isopropanol solution was placed in a 250 ml three-neck round bottom flask fitted with a reflux condenser and was stirred and heated to reflux for 1 hour. To this refluxing solution, 6.355 g triethanolamine in 50 ml of dry isopropanol was slowly added to the refluxing alkoxide solution. The reaction mixture becomes translucent and then eventually forms into a milky white suspension. The solution/suspension was refluxed for one-half hour and then 0.767 g of water diluted in 100 ml dry isopropanol was added dropwise followed by an additional one-half hour of refluxing. The isopropanol was distilled off until the remaining volume was about 50 ml and the flask was allowed to cool to room temperature. Upon removal of virtually all of the reaction solvent by rotary evaporation, a white solid was isolated. This solid was pulverized in a mortar and pestle to give a powdered precursor composition that is soluble in polar solvents such as water, methanol, ethanol, etc.

The above precursor compositions are useful in making preceramic liquids for the manufacture of rare earth metal oxide ceramic objects. The properties of a particular preceramic liquid primarily depends upon the ratio of the weight of the precursor composition to that of the solvent, although as shown above other factors such as heat treatment can have an effect. Below in Tables 2 and 3, several exemplary weight/weight ratio ranges are given for two different precursor composition/solvent combinations for preceramic liquids having a wide range of viscosity properties and thus uses.

TABLE 2

Ratio Ranges of 2-Ethylhexanoic Acid-Ytterbium
Precursor Composition to Cyclohexane Solvent, Properties
of Preceramic Liquid and Use.

| W/W Ratio Range of Yb Precursor:Cyclohexane | Properties of Preceramic Liquid | Use |
|---|---|---|
| 85:15–40:60 | low to high viscosity liquid | adhesive |
| 85:15–65:35 | high viscosity liquid | fiber making |
| 75:25–1:99 | low viscosity liquid | spray coating |
| 92:8–83:17 | highly viscoelastic mass | casting/molding |

TABLE 3

Ratio Ranges of Triethanolamine-Ytterbium
Precursor Composition to Water Solvent, Properties of
Preceramic Liquid and Use.

| W/W Ratio of Precursor:Solvent | Properties of Preceramic Liquid | Use |
|---|---|---|
| 72:28–62:38 | paste to viscous liquid | adhesive |
| 70:30–65:35 | viscous liquid | fiber making |
| 69:31–10:90 | low-medium viscous liquid | spray coating |
| 80:20–72:28 | sticky mass to highly viscous liquid | molding/casting |

Table 2 should serve as a guide to making preceramic liquids comprising a rare earth metal precursor composition in which 2-ethylhexanoic acid is the complexing agent and a non-polar hydrocarbon, such as cyclohexane, is the solvent. Likewise, Table 3 should serve as a guide to making preceramic liquids comprising a rare earth metal precursor composition in which triethanolamine is the complexing agent and the solvent is a polar liquid, such as water. Given this disclosure, one skilled in the art would readily understand that the specific ratio ranges given can vary depending on the precursor and solvent used and the properties desired of the preceramic liquid. Therefore, all such variations are considered by the inventor to be within the scope of the present invention.

Formation of rare earth metal oxide ceramics using a preceramic liquid is straightforward and is carried out in the following manner. The preceramic liquid is shaped, molded, extruded, sprayed or otherwise manipulated into the desired form of the final ceramic object. The preceramic liquid is allowed to harden or cure by the evaporation of the solvent to form a green ceramic. The time needed for the formation of the green ceramic varies depending on the volatility of the solvent and the physical dimensions of the desired shape. For example, extruded fibers made of a preceramic liquid in which the non-polar solvent is highly volatile, such as pentane, the hardened green ceramic forms within a minute or less at room temperature due to the volatility of the solvent and the high surface area of the fiber shape. In contrast, a molded solid object made of preceramic liquid in which water is the solvent may take several hours to days to completely harden into the green ceramic object. The time required for the formation of the green ceramic may be decreased by lightly heating thus increasing the rate of evaporation of the solvent. This additional step is preferred when the solvent used to make the preceramic liquid is water.

Once the green ceramic is formed, (i.e. the solvent is substantially evaporated) the remaining non-volatile organic compounds are "burnt-out" in give an unsintered metal oxide ceramic. The burning out process is a controlled oxidation of the non-volatile organic compounds giving volatile by-products, such as carbon monoxide, carbon dioxide, and water thereby generating a metal oxide ceramic. This first step is typically carried out in air to below 340° C. for about 10 to 12 hours and subsequently under a substantially oxygen free or low oxygen (1–5% $O_2$) containing atmosphere. The green ceramic is slowly heated in a furnace to a temperature below 900° C. and held there for more than one hour. The rate of the increase in temperature of the furnace should not be so fast as to cause cracks or other defects in the final ceramic. The preferred rate should not exceed about 20° C./min and is preferably about 10° C./min. After this initial heat treatment, the furnace is cooled to a temperature of about 750° C. and the atmosphere is allowed to changed to ambient air to oxidize any remaining carbon containing compounds. The temperature is maintained for about 6 to 12 hours or until the rare earth oxide is substantially free of carbon compounds. It is at this point that the green ceramic has finally been transformed into an unsintered ceramic object which is ready to be sintered.

The purpose of the sintering process is to relieve internal stress within the ceramic and to increase the density of the microcrystals of rare earth oxide that constitute the ceramic. Elevated temperatures greater than about 1000° C. are required to achieve this and typically the sintering temperature is in the range between about 1200° and 1600° C. The oven is held at the final sintering temperature for at least one hour or longer. Typically the sintering temperature for fibers is about is two hours, however larger ceramic article require longer sintering times. At the end of the sintering time period, the furnace is turned off and allowed to cool to room temperatures over several hours. The color of the rare earth oxide ceramic depends on the rare earth elements present, for example ytterbium oxide is typically white in color, although other colors such as faint pink (erbium oxide) or faint blue(neodymium oxide) are possible.

The following specific embodiments and examples of the use of the precursor composition are intended to illustrate the principals of the present invention which is defined in the claims.

Example 5: Preparation of Erbium Oxide Fibers Using a Cyclohexane Based Preceramic Liquid: Under a dry, inert atmosphere (i.e. nitrogen) 575.3 g of a 0.256M erbium isopropoxide/isopropanol solution was placed in a 2 liter three neck round bottom flask fitted with a reflux condenser and was stirred and heated to reflux for about 1 hour. To this refluxing solution, 25.03 g 2-ethylhexanoic acid in 144.8 g of dry isopropanol was added dropwise. The reaction mixture becomes translucent and then eventually turns into a milky white suspension. The solution/suspension was refluxed for 1 hour and then 3.12 g of water diluted in 70 ml of dry isopropanol was added dropwise followed by and additional hour of refluxing. The flask was allowed to cool to room temperature and the solvent removed using vacuum rotary evaporation using a 50° C. water bath. Upon removal of virtually all of the reaction solvent, a pink-rosy layer of solid was isolated on the flask walls. The 2 liter flask was placed in a 60° C. oven to drive off all of the remaining solvent. The resulting brittle mass was powdered in a mortar and pestle. The powder was heat treated in air at about 200° C. for about 12 hours to give the heat treated precursor composition. The color of the precursor composition powder changes to an orange color during this process.

About 5.00 g of the orange precursor composition and about 2.123 g of cyclohexane solvent were thoroughly mixed together to give a viscous preceramic liquid having a weight ratio of precursor:solvent of about 70.2:29.8. Air bubbles were then removed from the preceramic liquid by lightly heating the preceramic liquid in a tightly sealed container and allowing the bubbles to naturally rise from the liquid. The substantially bubble free preceramic liquid was extruded from a fiber die having an opening of about 50 mm ($5.0 \times 10^{-5}$ m) and the green fiber was picked up with a winding speed of about 25.5 m/min. Approximately 900 meters of green ceramic fiber was spun. The green ceramic fiber was heat treated in ambient air for about 12 hours at approximately 250° C. and then for about 4 hours at approximately 300° C. The fiber was transferred to a furnace and heated to a maximum temperature of about 900° C. for about 1 hour under an atmosphere of nitrogen. The furnace was cooled to about 750° C. and the atmosphere was changed to air and held at that temperature for about 10 hours. During this process the green fiber was transformed into smooth, pinkish, transparent vitreous fiber having an average diameter of approximately 20–30 Mm ($2.0 \times 10^{-5}$–$3.0 \times 10^{-5}$ m).

The fiber was sintered and densified by heating to about 1300° C. for approximately 1 hour. The microcrystalline grain size of the sintered fiber ranges from 0.05 to 0.1 Mm ($5 \times 10^{-8}$ to $1 \times 10^{-7}$ m). The tested tensile strength of the fiber is about 350±100 MPa. The fiber is able to survive high temperatures (e.g. an oxygen/methane flame) without melting or deformation. The average microcrystalline grain size of the fiber after being subjected to these high temperatures remains below about 1 Mm ($1 \times 10^{-6}$ m). The emission spectra of the heated fiber exhibits multiple wavelength bands at approximately 550, 675, 825, 975, and 1550 nm (1 nm=$1 \times 10^{-9}$ m).

Example 6: Preparation of Ytterbium Oxide Fiber Using a Water-Based Preceramic Liquid: Under a dry, inert atmosphere (i.e. nitrogen) 59.97 g of a 0.60M ytterbium isopropoxide/isopropanol solution was placed in a 250 ml three neck round bottom flask fitted with a reflux condenser and was stirred and heated to reflux for 1 hour. To this refluxing solution, 6.355 g triethanolamine in 63 ml of dry isopropanol was added dropwise. The reaction mixture becomes translucent and then eventually turns into a milky white suspension. The solution/suspension was refluxed for 1 hour and then 0.767 g of water diluted in 20 ml dry isopropanol was added dropwise followed by an additional hour of refluxing. The solution becomes a thick paste at this point. The flask was allowed to cool to room temperature and the solvent was removed using rotary evaporation in air. Upon removal of virtually all of the reaction solvent, a white solid layer was isolated on the walls of the flask. This white solid was dissolved in 50 ml hexane to give a clear, yellowish, viscous solution. The solution was transferred to an open evaporating dish, such as a large petri dish, and the solvent was allowed to evaporate under ambient conditions. The resulting brittle mass, which was colorless and transparent, was powdered in a mortar and pestle to give the powdered precursor composition that is soluble in water.

About 4.20 g of the precursor powder was thoroughly mixed with about 1.84 g of water to give a clear preceramic liquid having a w/w ratio of about 69.5:30.5. Trapped air bubbles were then removed. The bubble free precursor liquid was transferred to a die having a hole of about 50 mm ($5.0 \times 10^{-5}$ m) and fiber was synchronously extruded onto a spindle to give the green ceramic. The green ceramic fiber was dried at about 110° C. for approximately 2 hours and then transferred to a furnace and heat treated in air by heating to approximately 200° C. over about 60–70 minutes. The fiber was then heated to approximately 750° C. and held at that temperature for about 10 hours. Full densification is achieved by further heat treatment to a final sintering temperature in the range of about 1300° to 1500° C. for about 5 hours. The microcrystalline grain size of the fiber ranges from about 0.1 to 0.5 mm ($1 \times 10^{-7}$ to $5 \times 10^{-7}$ m) after the final sintering process.

One skilled in the ceramic art would know, given the present disclosure, that a wide variety of uses are possible for the preceramic liquid. Clearly ceramic objects can be made having a variety of shapes are possible by such conventional techniques of casting, molding, etc. In the first illustrative example given below, the preceramic liquid is used for joining rare earth metal oxide fibers and other ceramic objects together without the addition of other elements or components. The preceramic liquid can also be used as a means of creating a thin film coating of rare earth metal oxide ceramic on surfaces as illustrated in the second example given below. It is to be understood that these examples are for illustrative purposes only and are not intended to limit the scope of the invention which is defined in the claims.

Example 7: Approximately 5.0 g of precursor powder prepared according to Example 1 was gradually added to about 7.5 g of cyclohexane with mixing thus forming a viscous clear preceramic liquid having a w/w ratio of about 40:60. The preceramic liquid was used to join two pieces of ytterbium oxide ceramic by applying the preceramic liquid to each piece, pressing the two pieces together and holding the two pieces together until the solvent of the preceramic liquid evaporates. The two ceramic pieces, connected together by green ceramic, were heat treated so as to give a single, substantially solid ceramic object.

Example 8: Approximately 5.0. g of precursor powder prepared according to Example 1 was gradually added into about 20.0 g of cyclohexane and with stirring forms a clear preceramic liquid having a w/w ratio of about 20:80. The preceramic liquid was sprayed through a standard air/liquid spray gun onto a cylindrical alumina tube instantaneously forming a thin adherent coating film of green ceramic on the tube's surface. The coated tube was heat treated so as to give a thin film of ytterbium oxide on the surface of the alumina tube.

The present invention has been described in relation to a limited number of examples which are for illustrative purposes and are not intended to limit the scope of the invention. Although a number of specific embodiments, methods and compositions have been described and illustrated herein, it will be apparent to those skilled in the art that further variations are possible. Thus, the present invention may be practiced otherwise than specifically described herein, and therefore is defined by the following claims.

What is claimed is:

1. A rare earth metal oxide ceramic precursor composition made by:

reacting a rare earth metal alkoxide with a complexing agent in a reaction solvent to give a mixture of complexing agent-alkoxide rare earth metal compounds in the reaction solvent;

hydrolyzing the mixture of complexing agent-alkoxide-rare earth metal compounds to give the rare earth metal oxide ceramic precursor composition mixed with the reaction solvent; and isolating the rare earth metal oxide ceramic precursor composition from the reaction solvent.

2. The rare earth metal oxide ceramic precursor composition recited in claim 1, wherein the precursor composition is soluble in polar solvents and wherein the complexing agent used to make the precursor composition is triethanolamine.

3. The rare earth metal oxide ceramic precursor composition recited in claim 1, wherein the precursor composition is soluble in non-polar solvents and wherein the complexing agent used to make the precursor composition is 2-ethylhexanoic acid.

4. The rare earth metal oxide ceramic precursor composition as recited in claim 1 wherein the complexing agent is selected from the group consisting of 2-ethylhexanoic acid and triethanolamine.

5. The rare earth metal oxide ceramic precursor composition as recited in claim 1 wherein the rare earth metal alkoxide comprises rare earth metals selected from the group consisting of cerium, praseodymium, neodymium, promethium, samarium, europium, gadolinium, terbium, dysprosium, holmium, erbium, thulium, ytterbium, lutetium and mixtures thereof, and the alkoxide is selected from the group of alkoxides consisting of straight chain, branched, and cyclic primary alkoxides having from 1 to 6 carbon atoms, straight chain, branched and cyclic secondary alkoxides having from 3 to 8 carbon atoms, and branched and cyclic tertiary alkoxides having from 4 to 8 carbon atoms.

6. The rare earth metal oxide ceramic precursor composition as recited in claim 1 wherein the reaction solvent is selected from the group of alcohols consisting of straight chain, branched, and cyclic primary alcohols having from 1 to 6 carbon atoms, straight chain, branched and cyclic secondary alcohols having from 3 to 8 carbon atoms, and branched and cyclic tertiary alcohols having from 4 to 8 carbon atoms.

7. A rare earth metal oxide ceramic precursor composition prepared by combining:

at least one rare earth metal alkoxide with;

a complexing agent in a reaction solvent to give a mixture of complexing agent-alkoxide rare earth metal compounds in the reaction solvent, wherein the mixture is hydrolyzed to provide the rare earth metal oxide ceramic precursor composition mixed with the reaction solvent, and wherein the rare earth metal oxide ceramic precursor composition is isolated from the reaction solvent;

wherein the precursor composition is not sensitive to conditions of temperature and relative humidity; and wherein the precursor composition is soluble in polar solvents.

8. The rare earth metal oxide ceramic precursor composition as recited in claim 7 wherein the complexing agent is selected from the group consisting of 2-ethylhexanoic acid and triethanolamine.

9. The rare earth metal oxide ceramic precursor composition as recited in claim 7 wherein the rare earth metal alkoxide comprises rare earth metals selected from the group consisting of cerium, praseodymium, neodymium, promethium, samarium, europium, gadolinium, terbium, dysprosium, holmium, erbium, thulium, ytterbium, lutetium and mixtures thereof.

10. The rare earth metal oxide ceramic precursor composition as recited in claim 7 wherein the alkoxide is selected from the group of alkoxides consisting of straight chain, branched, and cyclic primary alkoxides having from 1 to 6 carbon atoms, straight chain, branched and cyclic secondary alkoxides having from 3 to 8 carbon atoms, and branched and cyclic tertiary alkoxides having from 4 to 8 carbon atoms.

11. The rare earth metal oxide ceramic precursor composition as recited in claim 7 wherein the reaction solvent is selected from the group of alcohols consisting of straight chain, branched, and cyclic primary alcohols having from 1 to 6 carbon atoms, straight chain, branched and cyclic secondary alcohols having from 3 to 8 carbon atoms, and branched and cyclic tertiary alcohols having from 4 to 8 carbon atoms.

12. A rare earth metal oxide ceramic precursor composition prepared by combining:

at least one rare earth metal alkoxide, wherein the rare earth metal alkoxide comprises rare earth metals selected from the group consisting of cerium, praseodymium, neodymium, promethium, samarium, europium, gadolinium, terbium, dysprosium, holmium, erbium, thulium, ytterbium, lutetium and mixtures thereof; with a complexing agent in a reaction solvent to give a mixture of complexing agent-alkoxide rare earth metal compounds in the reaction solvent, wherein the complexing agent is selected from the group consisting of 2-ethylhexanoic acid and triethanolamine, wherein the mixture is hydrolyzed to provide the rare earth metal oxide ceramic precursor composition mixed with the reaction solvent, and wherein the rare earth metal oxide ceramic precursor composition is isolated from the reaction solvent;

wherein the precursor composition is not sensitive to conditions of temperature and relative humidity; and wherein the precursor composition is soluble in polar solvents.

* * * * *